United States Patent [19]
Moss

[11] Patent Number: 5,147,334
[45] Date of Patent: Sep. 15, 1992

[54] CATHETER FOR CHOLANGIOGRAPHY

[76] Inventor: James P. Moss, 4001 Kresge Way, Louisville, Ky. 40207-4604

[21] Appl. No.: 636,739

[22] Filed: Jan. 2, 1991

[51] Int. Cl.$^5$ ............................................. A61M 25/00
[52] U.S. Cl. .................................... 604/264; 128/658
[58] Field of Search .............. 604/264, 265, 266, 43, 604/96, 280, 51; 128/657, 658, 656

[56] References Cited

U.S. PATENT DOCUMENTS

| | | | |
|---|---|---|---|
| 3,828,767 | 8/1974 | Spiroff | 604/280 |
| 3,918,456 | 11/1975 | Patel | 604/104 |
| 4,263,917 | 4/1981 | Moss | 128/656 |
| 4,280,500 | 7/1981 | Ono | 604/280 |
| 4,581,390 | 4/1986 | Flynn | 523/112 |
| 4,696,668 | 9/1987 | Wilcox | 604/28 |
| 5,015,232 | 5/1991 | Maglinte | 604/96 |

FOREIGN PATENT DOCUMENTS

| | | | |
|---|---|---|---|
| 0314281 | 5/1989 | European Pat. Off. | 604/280 |
| 3740288 | 4/1989 | Fed. Rep. of Germany | 604/280 |
| 1443881 | 12/1988 | U.S.S.R. | 604/280 |

*Primary Examiner*—C. Fred Rosenbaum
*Assistant Examiner*—Adam J. Cermak
*Attorney, Agent, or Firm*—Larson & Taylor

[57] ABSTRACT

A cholangiographic catheter is provided for delivering a contrast fluid for use in X-rays. The device comprises an elongated tube with a curved section. The curved section has a tapered tip and a means for discharging a fluid in a directional flow for reaching the proximal or intraheptic bile ducts as well as the duodenum. In a preferred embodiment, the catheter would have a first set of holes on the curved section and a second set of holes that are smaller than the first located below the first. This would allow for greater control of dispersion of contrast fluid used in X-rays. The catheter would be made of a medical elastomer with memory so that the catheter may maintain the shape of the curved section after the catheter has been inserted into the body.

3 Claims, 1 Drawing Sheet

CATHETER FOR CHOLANGIOGRAPHY

FIELD OF THE INVENTION

This invention relates generally to catheters and more specifically, to an improved catheter for cholangiography.

BACKGROUND OF THE INVENTION

Of the catheters manufactured today, there appear to be none which are designed and constructed in such a manner as to make them ideal for use in cholangiography. A cholangiographic catheter would have to be placed through the cystic duct of a patient and then enter into the common bile duct. Due to the sensitive nature of this region, i.e. the possibility of puncturing, commercially available catheters are not suitable. Several examples of catheters are disclosed in U.S. Pat. Nos. 4,836,441; 4,883,474; 4,886,506; 4,887,996; 4,913,683; 4,279,252; 4,747,840; 3,938,501; 4,801,297; 4,117,836; and 4,563,181. All of these patents would be unusable in cholangiography due to: the difficulty of inserting the catheter through the cystic duct, the potential for tearing the common bile duct, and the inability to direct the flow of inserted material away from the catheter tip.

Only one U.S. Patent was found which disclosed the ability to control the spray of inserted material. U.S. Pat. No. 3,828,767 (Spiroff) discloses an angiographic catheter which is used in the heart. The Spiroff device is specifically designed with varying size holes to discharge a uniform cloud of fluid around the tip of the catheter. While this uniform cloud serves a useful purpose for angiographic use, it is not effective for use in cholangiography The catheter disclosed in the Spiroff patent would have difficulty passing through the cystic duct well of a patient due to the lack of an effective taper in the tip.

Although all of the above devices relate to catheters the have the various disadvantages mentioned above.

SUMMARY OF THE INVENTION

According to the invention, a cholangiographic catheter is provided which overcomes the above mentioned problems. The catheter comprises an elongated tube with a curved section. The curved section has a tapered tip and a means for discharging a fluid in a directional flow for reaching the proximal or intrahepatic bile ducts as well as the duodenum.

In a preferred embodiment, the catheter would have a first set of holes on the curved section and a second set of holes that are smaller than the first located below the first. This would allow for greater control of dispersion of contrast fluid used in X-rays. The catheter would be made of a medical elastomer with memory so that the catheter may maintain the shape of the curved section after the catheter has been inserted into the body.

The curved section of the catheter allows for a much better angle of insertion of the catheter into the cystic duct. The taper provides for an easier insertion into a surgical opening and also avoids the problem of the catheter being caught by valve-like folds of mucosa in the cystic duct. The arrangement of the holes in the curved section of the catheter improves the ability of the catheter to direct a contrast fluid into the proximal or intrahepatic bile ducts and the duodenum, thus making them more visible on an X-ray.

Other features and advantages of the invention will be set forth in, or apparent from, the following detailed description of the preferred embodiment of the invention.

DESCRIPTION OF THE PREFERRED EMBODIMENTS

Figure 1:
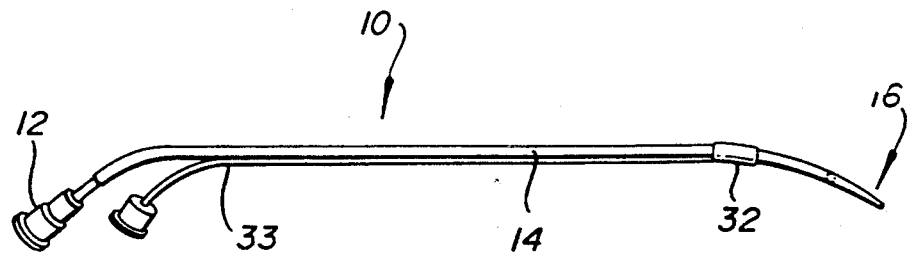
FIG. 1 is a side elevational view of a catheter constructed in accordance with a preferred embodiment of the invention.
Figure 2:
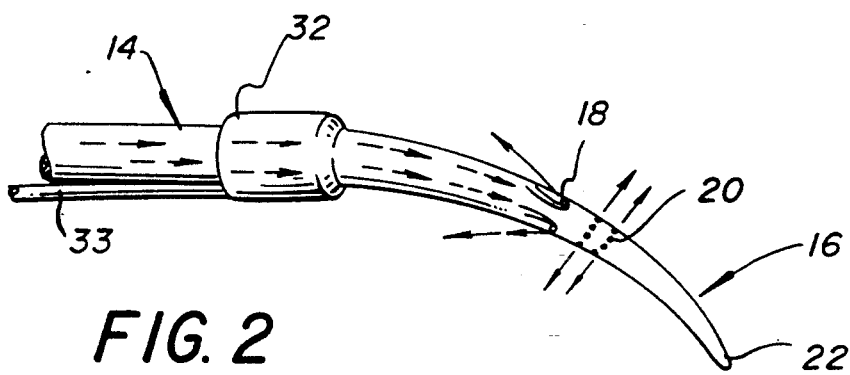
FIG. 2 is a detailed view of the tip of the catheter of FIG. 1.
Figure 3:
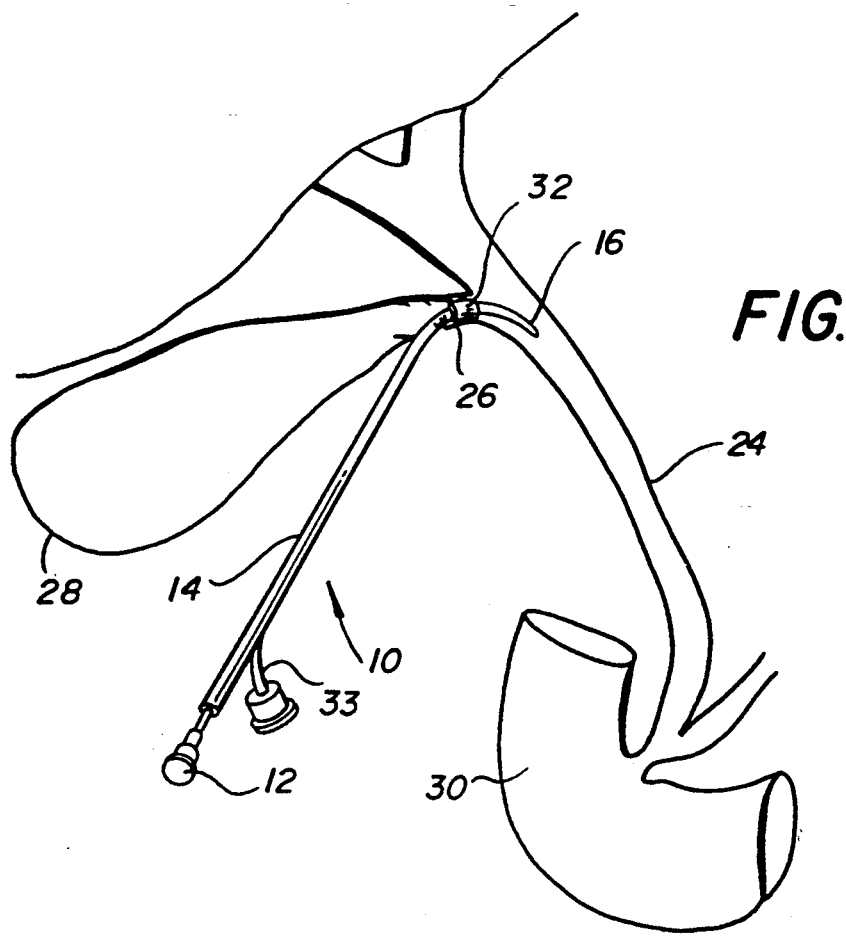
FIG. 3 is a plan view of the catheter of FIG. 1 in use.

Referring to FIGS. 1, 2, and 3, a catheter constructed in accordance with a preferred embodiment of the invention is shown. The catheter 10 is composed of a detachable coupling 12, a straight tubular section 14 and a curved and tapered tip 16. In a preferred embodiment, the overall length of the catheter is 20 cm and has an outside diameter of 16 Fr. The catheter 10 is constructed of a medical elastomer with memory. The memory in the elastomer provides the ability to straighten bent tip 16 so that it ma be introduced into the body through a conventional hollow tube and will return to its original bent shape after removal of the hollow tube. The catheter 10 tapers down gradually, in the curved tip region 16, to a soft end 22 as may be seen in FIG. 2. Soft end 22 is specifically designed not to perforate the walls of the bile duct 24. The taper is vital to the initial insertion and passage of the catheter 10 through a surgical opening into the cystic duct 26. On the curved tip region 16 is a plurality of larger holes or slits 18 which are used to direct fluid introduced into the catheter 10 in a direction away from the end 22 of catheter 10. Located longitudinally closer to the end 22 is a plurality of smaller holes 20. While the majority of fluid exits via holes or slits 18, some fluid emerges from holes 20 and is ejected perpendicular to the axis of tip 16. The arrangement of holes 18 and 20 help to direct a portion of the fluid into the proximal or intrahepatic bile ducts located above catheter tip 16; thus increasing visibility in an X-ray. Present catheters with a single end hole direct the fluid towards and into the duodenum 30, located below the catheter tip so that too often the higher bile ducts which join the liver are poorly seen. In order to seal off the cystic duct 26 and gall bladder 28 there is provided an inflatable balloon 32 which is connected to an elongated tube 33 attached to the straight tubular section 14. After the catheter is in place as shown in FIG. 3, the balloon is inflated through tube 33 to seal off the cystic duct 26 leading to gall bladder 28.

Considering the overall operation of the catheter 10, FIG. 3 depicts the catheter 10 in use. First the detachable syringe 12 is attached to the straight section 14 of the catheter 10. Next the catheter tip 16 is inserted into the cystic duct 26 of the gall bladder 28. The curve in the tip 16 of catheter 10 allows for a much better angle of insertion of the catheter 10 into the cystic duct 26 especially when removing the gall bladder 28 by a laparoscopic technique. The tapered end can be more easily inserted into the surgical opening in the cystic duct 26 than presently available olive shaped or blunt tipped catheters. This tapered tip 16 allows the catheter to pass readily through the valve-like folds of mucosa in the cystic duct 26 and thus avoid being entrapped by the mucosa. As may be seen in FIG. 3, the catheter 10 is inserted so as to allow the tip 16 to enter the common bile duct 24. The curve in catheter 10 is vital in the reaching of this duct 24. When the catheter 10 is properly positioned, a fluid composed of X-ray medium is forced out of holes 18 and 20 help to direct the fluid not only to come into contact with the duodenum 30 below, but also the proximal and intrahepatic bile ducts above. The balloon 32 blocks off the cystic duct 26 so that the X-ray medium will pass into the intrahepatic bile ducts rather than into the cystic duct. This enables clearer X-rays to be taken than prior art devices.

Although the present invention has been described to specific exemplary embodiments thereof, it will be understood by those skilled in the art that variations and modifications can be effected in these exemplary embodiments without departing from the scope and spirit of the invention.

What is claimed is:

1. A cholangiographic catheter comprising: an elongated tube having proximal and distal end portions, a curved section on the distal end portion and said curved section having a tapered tip at the distal end of said curved section; a first and second plurality of holes disposed radially on said curved section for discharging a fluid in a directional flow for reaching the proximal of intrahepatic bile ducts as well as the duodenum, said second plurality of holes being smaller than said first plurality of holes; a soft and blunt distal end on said tapered tip; and a detachable coupling attached to the proximal end of said elongated tube.

2. The catheter recited in claim 1 wherein said catheter is composed of a medical elastomer with memory for maintaining the shape of said curved section.

3. The catheter recited in claim 1 and further including an inflatable balloon disposed adjacent the curved section of the elongated tube.

* * * * *